United States Patent
Orth et al.

(10) Patent No.: US 7,291,476 B1
(45) Date of Patent: Nov. 6, 2007

(54) O-ACETYLTRANFERASES

(75) Inventors: Kim Orth, Dallas, TX (US); Sohini Mukherjee, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 11/433,212

(22) Filed: May 11, 2006

(51) Int. Cl.
*G01N 33/53* (2006.01)
(52) U.S. Cl. .................. 435/7.1; 435/7.2; 435/7.92; 436/545; 436/546; 436/88; 436/173
(58) Field of Classification Search ............... 435/7.1, 435/7.2, 7.92; 436/545, 546, 88, 173
See application file for complete search history.

(56) References Cited

OTHER PUBLICATIONS

Schmeck et al. J. Immunology 2005 vol. 175, p. 2843-2850.*
Brooks et al. Curr. Opin. Cell Biol. 2003 vol. 15, p. 164-171.*
Roth Ann. Rev. Biochem. 2001 vol. 70 p. 81-120.*

* cited by examiner

*Primary Examiner*—Long V. Le
*Assistant Examiner*—Jacob Cheu
(74) *Attorney, Agent, or Firm*—Richard Aron Osman

(57) ABSTRACT

A post-translational modification of a predetermined protein expressed by a cell is detected by specifically detecting an O-acetylation of a serine, threonine or tyrosine residue of the protein as an indication of the post-translational modification. The detection may employ antibodies that specifically bind an O-acetylated protein expressed by the cell, wherein the specific binding is dependent on the presence of an O-acetylated serine, threonine or tyrosine residue in the protein.

13 Claims, No Drawings

O-ACETYLTRANFERASES

This work was supported by NIH Federal Grant No. ROI-AI056404. The U.S. government may have rights in any patent issuing on this application.

BACKGROUND OF THE INVENTION

The field of the invention is post-translational modifications of serine and threonine residues of proteins by O-acetyltransferases.

The bacterial pathogen *Yersinia pestis* is the causal agent of plague, also known as the Black Death (Hinnebusch, 2005). Two related pathogens *Yersinia pseudotuberculosis* and *Yersinia enterocolitica* are the causal agents for gastroenteritis (Viboud, 2005). All three *Yersinia* spp. harbor a virulence pathogen that encodes a Type III secretion system and secrete effector proteins, referred to as Yops (Yersinia outer proteins) (Viboud, 2005). Yops are delivered by this system into a eukaryotic cell to cripple the host defense system (Orth, 2002; Navarro, 2005). The Yersinia effector protein, YopJ, has been shown to disrupt signaling essential for eukaryotic cells to elicit an immune response by inhibiting the MAPK and the NFκB signaling pathways (Viboud, 2005; Orth, 2002; Orth, 1999). YopJ also inhibits MAPK signaling in yeast, thus demonstrating that it targets a signaling mechanism that is evolutionarily conserved (Yoon, 2003). Further studies demonstrate that YopJ contains a catalytic domain that is similar to Clan CE of cysteine proteases, which includes the adenoviral protease (AVP) family and the ubiquitin-like protein protease (Ulp-1) family (Orth, 2000). Mutation of the putative catalytic cysteine residue to an alanine in YopJ (YopJ-C172A) abolishes its ability to inhibit the MAPK and the NFκB signaling pathways (Orth, 2000). YopJ binds MAPK kinases, including MKK1, MKK3, MKK4, MKK5, and the related kinase that activates the NFκB pathway, IκB kinase β (IKKβ) and prevents their activation (Orth, 1999).

We show that YopJ is an O-acetyltransferase that inactivates kinases by acetylating key serine and threonine residues in the activation loop, blocking phosphorylation. We report that YopJ is one example of a previously unrecognized family of serine/threonine O-acetyltransferases used by plants, animals and their pathogens to post-translationally modify proteins and regulate their activity.

The disclosed post-translational ser/thr O-acetyltransferase activity (acetyl transfer to a serine or threonine residue of substrate protein) has never been reported. Direct O-acetylation of serine residues has been reported by aspirin-like drugs (e.g. Kalgutkar, 1998), and one mechanistic model of an acetylcholinesterase employs a catalytic serine to accept an acetyl, and then immediately discharge it by hydrolysis to recycle the esterase (e.g. Stojan, 2004).

BRIEF SUMMARY OF THE INVENTION

The invention provides methods and reagents for detecting O-acetylation of a substrate protein of an O-acetyltransferase, wherein O-acetylation of a serine, threonine or tyrosine residue of the protein is specifically detected.

The specific detecting step may comprise contacting the protein with an antibody that specifically binds O-acetylated serine, threonine, or tyrosine, and determining that the antibody specifically binds the residue. In other embodiments, the specific detecting step comprises mass spectrometry analysis of the protein, or tracking a labeled acetyl.

The method can be used to detect O-acetylation under a first physiological condition, in comparison to a control O-acetylation detected under a second physiological condition.

The method can be used to detect O-acetylation that competes with a different posttranslational modification at the residue such as phosphorylation, glycosylation ubiquitination, and SUMOylation. In specific embodiments, the protein is a kinase (e.g. MAP kinase kinase and IKKβ).

In one embodiment, the method comprises the prior step of: incubating a mixture comprising the protein, the O-acetyltransferase, and an acetyl under conditions wherein the O-acetyltransferase transfers the acetyl to the serine, threonine or tyrosine residue of the protein to form said O-acetylation. The acetyl can be radiolabeled. In various embodiments, the acetyltransferase comprises a catalytic domain of a Clan CE cysteine protease, and may be from a bacterium of a genus selected from the group consisting of *Yersinia, Aeromonas, Salmonella, Vibrio, Bartonella, Ralstonia, Pseudomonas, Xanthomonas, Erwinia*, and *Rhizobium*. The mixture may further comprise a candidate agent, and the specifically detected O-acetylation is reduced relative to a control, identifying the candidate agent as an inhibitor of the O-acetyltransferase. In another specific embodiment, the mixture further comprises an O-acetyltransferase inhibitor selected from the group consisting of 5,5'-dithiobis-(2-nitrobenzoic acid), 2,2'-dithiopyridine, p-mercuribenzoate, N-(4-dimethylamino-3,5-dinitrophenyl)-maleimide, N-ethylmaleimide, iodoacetamide, and iodoacetate or a chemical inhibitor from an O-acetyltransferase inhibitor screen (herein), and the specifically detected O-acetylation is reduced relative to a control. The detecting step can comprise specifically detecting a physiological change predetermined to be correlated with the reduced O-acetylation.

Another aspect of the invention is an isolated antibody that specifically binds an O-acetylated protein expressed by a cell, wherein the specific binding is dependent on the presence of an O-acetylated serine, threonine or tyrosine residue in the protein. In specific embodiments, the antibody specifically binds an O-acetylated serine or tyrosine residue in a MAP kinase kinase or IKK-β.

DETAILED DESCRIPTION OF SPECIFIC EMBODIMENTS

The inventors have discovered a novel post-translational modification where a substrate protein is acetylated by an O-acetyltransferase at a serine (Ser), threonine (Thr) and/or tyrosine (Tyr) residue. The invention provides methods and reagents, such as specific antibody reagents, for specifically detecting O-acetylation of a Ser, Thr, or Tyr residue of a substrate protein, distinct from the transferase.

The subject transferase stably and catalytically transfers an acetyl from a donor to a substrate protein, as distinct from drug-based modes of acetylation, or esterases wherein in the course of cleaving a substrate ester, a catalytic serine of the enzyme itself may temporarily accept and then discharge by hydrolysis of an acetyl. To the extent a substrate-inhibited form of such an esterase is prevented from discharging the acetyl (e.g. Stojan, supra), the enzyme is still not an acetyl substrate as required by our claims.

Various suitable methods can be used to detect O-acetylation of a Ser, Thr, or Tyr residue of the protein including mass-spectroscopy analysis, radiolabeling, antibody labeling, etc. In one method the detecting step comprises contacting the protein with an antibody that specifically binds O-acetylated Ser, Thr, or Tyr, and determining that the antibody specifically binds the residue. The antibody binding can be detected by any suitable method such as ELISA, immunohistochemistry, immunofluorescence, Western Blot, affinity purification, etc.

The method may comprise the prior step of incubating a mixture comprising the substrate protein, the O-acetyltransferase, and a functional acetyl donor (e.g. acetyl CoA, acetyl phosphate, etc.) under conditions wherein the O-acetyltransferase transfers the acetyl to a Ser, Thr, or Tyr residue of the protein to form the O-acetylation. The acetyl can be radiolabeled to facilitate detection of the O-acetylation. The mixture may. comprise cells in vitro, in vivo, or in situ that comprise the substrate protein, or fractions or lysates of the cells. The substrate protein may be recombinantly expressed by the cell, optionally as a fusion protein for example with a protein label (e.g. GFP) or with a tag protein (e.g. FLAG tag), etc, to facilitate detection, purification, etc. In some embodiments, the mixture is cell free and comprises a purified substrate protein. The O-acetyltransferase may be from the same species as the substrate protein, or alternatively is from a pathogen that infects the species. In various methods the O-acetyltransferase is recombinant or purified. In a specific embodiment, the O-acetyltransferase comprises a catalytic domain of a Clan CE cysteine protease. Examples of Clan CE cysteine proteases include YopJ, the adenoviral protease (AVP) family, and the ubiquitin-like protein protease (Ulp-1) family [Orth, 2000]. In specific embodiments, the O-acetyltransferase is from a bacterium of a genus selected from *Yersinia, Aeromonas, Salmonella, Vibrio, Bartonella, Ralstonia, Pseudomonas, Xanthomonas, Erwinia,* and *Rhizobium.*

The method can be used to compare differential posttranscriptional O-acetylation of proteins of different cells or organisms, and under different physiological conditions. A variety of conditions can be tested and compared including pathogen-infected and uninfected cells or organisms, drug-treated and untreated cells or organisms, transformed and untransformed cells, hypoxic and non-hypoxic cells, cells of varied differentiation (e.g. mature and immature cells, quiescent and dividing cells, differentiated and non-differentiated cells (e.g. stem and progenitor cells)), etc. Accordingly, in a specific application of the method, the detected O-acetylation occurs under a first physiological condition, and is compared with a control O-acetylation that occurs under a second physiological condition.

The method can be used to detect an O-acetylation of a Ser, Thr, or Tyr residue that competes with a different posttranslational modification at the residue, such as phosphorylation, ubiquitination, SUMOylation, and glycosylation and sulfonation. The method is of particular interest when the O-acetylation competes for a post translational modification that activates the substrate protein. For example, in certain embodiments, the O-acetylated protein is an inactivated kinase that is normally activated by phosphorylation of the residue. Examples of kinases that are inactivated by post-translational O-acetylation include MAP kinase kinases and IKKβ.

The method can be used to screen for inhibitors of a Ser, Thr and/or Tyr O-acetyltransferase by incubating a mixture comprising the O-acetyltransferase, a substrate protein thereof, and a candidate agent under conditions wherein but for the presence of the agent, the O-acetyltransferase induces a control O-acetylation of a Ser, Thr or Tyr residue of the substrate protein; and detecting a reduced O-acetylation of the residue relative to the control, which identifies the candidate agent as an inhibitor of the O-acetyltransferase.

Examples of candidate agents include inhibitors of enzymes that utilize catalytic cysteine residues, such as 5,5'-dithiobis-(2-nitrobenzoic acid), 2,2'-dithiopyridine, p-mercuribenzoate, N-(4-dimethylamino-3,5-dinitrophenyl)-maleimide, N-ethylmaleimide, iodoacetamide and iodoacetate; inhibitors of Clan CE cysteine proteases; etc. Alternative inhibitor classes include dominant negatives, inhibitory YopJ peptides, intrabodies, inhibitory serine analogs, and yeast-assayable library inhibitors (below). Identified inhibitors are then preferably confirmed to act on the acetylase, rather than as a deacetylating reagent.

The method can be used to detect reduced O-acetylation of a substrate protein wherein a mixture comprising the O-acetyltransferase, a substrate protein thereof, and an O-acetyltransferase inhibitor are incubated, and the specifically detected O-acetylation is reduced relative to a control. In one embodiment, the O-acetyltransferase inhibitor is selected from the group consisting of 5,5'-dithiobis-(2-nitrobenzoic acid), 2,2'-dithiopyridine, p-mercuribenzoate, N-(4-dimethylamino-3,5-dinitrophenyl)-maleimide, N-ethylmaleimide, iodoacetamide, and iodoacetate. The detecting step may comprise specifically detecting a physiological change predetermined to be correlated with the reduced O-acetylation.

The detection steps in the above-described methods may employ an antibody that specifically binds an O-acetylated Ser, Thr, or Tyr residue of a protein. In one embodiment, the antibody binds an O-acetylated Ser, Thr, or Tyr residue independent of the specific sequence of the substrate protein. Methods for making antibodies that bind modified residues of proteins, independent of protein sequence are well-known in the art (e.g. Qiang, 2005) and are described in Example 2. These antibodies can also be used to identify O-acetyltransferases and their substrates. Upon detecting O-acetylation of a substrate protein with the antibody, the corresponding O-acetyltransferase can be identified using methods such as two-hybrid analysis to determine proteins that interact with the substrate protein.

In another embodiment, the antibody binds an O-acetylated Ser, Thr, or Tyr residue, and is dependent on the specific sequence of the substrate protein. Such sequence-dependent antibodies can be made by generating synthetic peptides of approximately 10-20 amino acids in length, blocking reactive side chains of the amino acids in which acetylation is not desired; and acetylating the desired Ser, Thr, and/or Tyr residue(s) using a suitable acetylating reagent (e.g. acetic anhydride). Alternatively, the blocking and acetylation steps may be avoided by incorporating the desired acetylated amino acid(s) into the peptide during the synthesizing step. For example, serine acetylated peptides are readily made by conventional synthesis incorporating commercially-available acetylated-serine into the peptide and foregoing the deblocking step for that residue. A host animal (e.g. mouse, rabbit, sheep, cow, etc.) is immunized with the acetylated peptide, again using conventional immunization protocols, and specific antibodies generated by the host animal are purified, typically by affinity purification to separate antibodies that specifically bind the O-acetylated peptide and not the corresponding unacetylated peptide, i.e. the specific binding of the antibody is dependent on the presence of an O-acetylated Ser, Thr, or Tyr residue.

Antibodies of particular interest specifically bind an O-acetylated residue in the activation loop of an enzyme, such as a kinase domain. In one embodiment, the antibody specifically binds an acetylated residue of an enzyme that is otherwise activated by post-transcriptional modification of the residue with a group other than an acetyl group, such as a phosphate group. In a specific example, the antibody specifically binds an acetylated Ser or Thr residue in the activation loop of an IKK or a Map kinase kinase (such as Ser 207 and Thr 211 of human MKK6).

Example 1: Yersinia YopJ Acetylates Ser/Thr Residues on MKKs and IKKβ and Inhibits Activation by Blocking Phosphorylation To elucidate the molecular mechanism utilized by YopJ, we have established a modified cell-free signaling system to recapitulate the inhibition of the MAPK and the NFκB signaling pathways by YopJ [Orth, 1999; Yoon, 2003; Orth, 2000; Palmer, 1999]. Membrane cleared cell lysates were harvested from HEK293 cells transfected with pSFFV empty vector (V), pSFFV-FLAG-YopJ (J) or pSFFVFLAG-YopJ-C/A (C/A). Lysates were incubated with (A) purified B-Raf for 10 min at 37° C. followed by immunoblotting with anti-phospho-ERK antibody. Mammalian ERK signaling was activated as demonstrated by the appearance of phosphorylated ERK. By contrast, activation of ERK signaling was diminished in cleared lysate isolated from cells transfected with YopJ. The catalytic activity in YopJ was required for this inhibition, because addition of B-Raf to cleared lysate isolated from cells expressing mutant YopJ-C172A led to activation of the ERK pathway.

For activation of the NFκB pathway, we incubated a purified active form of recombinant TRAF6 (T6RZC; [Deng, 2000]) to both control and YopJ-C172A cleared lysates for 10 min at 37° C. followed by immunoblotting with anti-phospho-IκB antibody. In both cases, the pathway was activated, as indicated by the phosphorylation of IκB. However, the addition of T6RZC to YopJ cleared lysate did not result in activation of the NFκB pathway. Similarly, when other exogenous stimuli (including NIK, MEKK1, and activated Ras-V12 membranes) were added to the lysates, signaling was blocked only in the YopJ lysates. No obvious changes were observed in the molecular weight or the stability of MKK1,2 or IKKβ in the lysates. These observations are consistent with previous genetic, microbial and cellular studies on the activity of YopJ and provide a method for analyzing inhibition of signaling by YopJ in vitro [Orth, 1999; Yoon, 2003; Orth, 2000; Palmer, 1999].

To test whether YopJ acts directly on the MKKs and IKKβ, we co-expressed a representative member of this group of kinases, human MKK6 (rMKK6), with either active YopJ or the catalytically inactive form of YopJ in bacterial cells, to produce rMKK6-J or rMKK6-C/A, respectively. We then assessed whether the various rMKK6s could be activated in our previously described in vitro signaling assay. Purified rMKK6, rMKK6-J and rMKK6-C/A were incubated with serum stimulated cleared lysate for 10 min at 37° C. followed by analysis with antiphospho-MKK6 antibody. rMKK6 was detected by immunoblotting with anti-Hisx4 antibody. Aldolase immunoblotblot was a load control for lysate. While both rMKK6 and rMKK6-C/A were robustly phosphorylated when added to cleared lysate, the rMKK6-J was not activated. Therefore, co-expression of YopJ with MKK6 in bacteria produced a kinase that cannot be activated by the upstream signaling machinery.

Biochemical studies on the YopJ inactivated rMKK6 were undertaken to determine the nature of the modifications, if any. Although all the rMKK6s were indistinguishable by SDS-PAGE and gel filtration, mass spectrometry revealed that the total mass of rMKK6-J was larger than that of either rMKK6 or rMKK6-C/A. The majority of YopJ inactivated rMKK6 showed an increase in mass of 126 amu, while smaller populations of rMKK6-J exhibited increases in mass of 84 amu or 42 amu. Based on these findings we hypothesized that YopJ altered the mass of rMKK6 by adding single, double or triple posttranslational modifications equal to a mass of 42 amu.

To determine the biochemical basis for the increase in rMKK6-J mass, we analyzed tryptic peptides for all three rMKK6s (rMKK6, rMKK6-J, rMKK6-C/A) using LC/MS/MS. After obtaining a complete data set for all the predicted tryptic peptides, we found that rMKK6-J, but not rMKK6 or rMKK6-C/A, contained two tandem peptides (peptide A: MKK6 195-210aa; peptide B: MKK6 211-224aa) modified by acetylation with a consequent increase of 42 amu for each peptide. In another partially cleaved tryptic peptide (MKK6 195-224 aa), which contained both peptides A and B, we observed multiple acetylated sites. Using tandem mass spectrometry, we discovered that peptide A in the rMKK6-J protein was modified by acetylation on Ser208 and peptide B was modified by acetylation on Thr211. In the third peptide, it appeared that Lys210 and Ser207 and/or Thr211 were modified by acetylation. Modification of the lysine contributes to the inefficient cleavage of this peptide by trypsin. Residues 195-224 map to the end of beta strand 9 and the activation loop in MKK6, which contains Ser207 and Thr211, the sites that are phosphorylated to activate MKK6. Although the serine and threonine residues are conserved throughout the MKK superfamily, the lysine residue is not.

The observation that YopJ covalently modifies the representative MAPK kinase, MKK6, by acetylation on the same residues that are used for activation of the kinase, provides a straightforward mechanism for the inhibition of MKKs and IKKβ: acetylation prevents phosphorylation.

YopJ can bind and inhibit MAPK kinases and IKKβ, and all of these kinases contain serine and/or threonine residues in their activation loop that must be phosphorylated to activate the kinase (Hardie, 1995). rMKK6 coexpressed with YopJ and shown to be actetylated at Ser207 and Thr211, was not phosphorylated by upstream signaling machinery. These observations confirm our finding that YopJ functions to modify the MKKs, without noticeably changing their migration pattern on SDS-PAGE.

To determine whether YopJ directly functions as an acetyltransferase, we performed a transferase reaction in the presence of 14C-labeled acetyl-CoA (Gu, 1997). Purified recombinant GST-YopJ or GST-YopJ-C/A was incubated with and without rMKK6 in the presence and absence of $^{14}$C-labeled acetyl-CoA for one hour at 30° C. Samples were separated by SDS-PAGE and analyzed by autoradiography. We observed that rMKK6 was modified with the $^{14}$C-labeled acetyl moiety only in the presence of GST-YopJ and the labeled acetyl donor $^{14}$C-acetyl-CoA. Purified recombinant GST-YopJ or GST-YopJ-C/A bound to glutathione sepharose beads was incubated with and without 200 pmoles rMKK6 in the presence and absence of 35 μM $^{14}$C-acetyl-CoA. YopJ beads were washed and supernatants were TCA precipitated, followed by measurement of the associated radiolabel. The $^{14}$C-label was associated with both rMKK6 and GST-YopJ. The beads were separated by SDS-PAGE followed by staining with Coomassie blue, and it was determined that rMKK6 associated with GST-YopJ was the source of the $^{14}$C-label. These studies demonstrate that YopJ requires both an intact catalytic site and acetyl-CoA to acetylate rMKK6. We did not observe any band in reactions that contained only GSTYopJ and 14C-acetyl-CoA, indicating that the charging of YopJ with a $^{14}$C-acetyl moiety might be transient, labile and/or dependent on the presence of a substrate or that the reaction proceeds through direct transfer. These experiments clearly show that YopJ acts as an acetyltransferase to modify rMKK6.

To demonstrate that the modification on rMKK6 by YopJ prevents activation via phosphorylation, we utilized our in vitro signaling system. Purified recombinant GST-YopJ and GST-YopJ-C/A were incubated with rMKK6 in the presence and absence of acetyl-CoA for one hour at 30° C., followed by incubation with serum stimulated cleared lysate for 10 minutes at 37° C. and immunoblot analysis with antiphospho-MKK6 antibody. We observed that pretreatment of rMKK6 only in the presence of both YopJ and acetyl-CoA diminished the ability of the upstream signaling machinery to activate rMKK6 by phosphorylation. These observations provide direct confirmation that acetylation of a MAPK kinase by YopJ prevents phosphorylation and, hence, activation of this kinase.

Example 2: Acetylated Ser/Thr/Tyr-Specific Antibodies.

Methods for the preparation of specific anti-O-acetylated serine, threonine, and tyrosine antibodies are prepared using a modification of methods for the preparation of specific anti-acetylated lysine antibodies (Qiang, 2005). Acetic anhydride is used to chemically acetylate hemocyanin of keyhole limpets (KLH) and bovine serum albumin (BSA). KLH (10 mg) or BSA (10 mg) is dissolved in 5 ml of 0.1 M $NaCO_3$. 200 µl of pyridine is added followed by 50 µl of acetic anhydride and incubated for 4 hr at 30° C. The acetylation reaction is stopped with 100 µl Tris-base, and the acetylated protein is purified using gel filtration.

Approximately 2 mg of AcKLH is used to immunize two rabbits. The rabbits receive booster immunizations at weeks 2 and 4, and serum is collected at week 6.

10 ml of L-serine agarose, L-threonine agarose, or L-tyrosine agarose beads (all from Sigma, St. Louis, Mo.) are washed and then suspended in 10 ml of pyridine/distilled water (1:10, v/v). Acetylation is carried out by adding 100 □L of acetic anhydride at 50° C. After 4 hours the beads are washed and packed into glass columns. 200 ml of the AcKLH immune serum is applied to each column, and the bound antibodies are eluted with glycine buffer. The eluted antibody fractions are tested by ELISA for immunoreactivity to acBSA, O-acetyl-serine, threonine or tyrosine is confirmed by RIA using radiolabeled acetyl.

Example 3: Yeast-Based O-Acetyltransferase Inhibitor Assay.

We have previously shown that YopJ affects the yeast MAP kinase pathways, and that expression of YopJ inhibits the ability of yeast to adapt to growth on high salt (Yoon, 2003). These assays are also used to test the effects of candidate O-acetyltransferase inhibitors for their ability to reverse the inhibitory effects of YopJ on yeast growth. The expression of YopJ is put under the control of a GAL1 promoter resulting in the induction of YopJ expression only when induced by growth on galactose. Yeast strains are grown on galactose plates to induce YopJ expression and transferred to galactose media containing 1 M sorbitol. Cells containing empty vector or the catalytically inactive YopJ (C/A), but not cells overexpressing wild type YopJ, are able to adapt and grow on media containing 1 M sorbitol (Yoon, 2003). The experiments are repeated supplementing the media containing 1 M sorbitol with compounds from a chemical library at concentrations ranging from 100 nm-10 mm.

Cells that express YopJ that are able to grow in 1 M sorbitol in the presence of a candidate agent are evaluated for reduced O-acetylation of Ser514 of yeast Pbs2p (Genbank accession no. NP012407) using antibodies that specifically bind the acetylated serine residue. Candidate inhibitors identified in the yeast screen are validated in an in vitro assay. Purified recombinant YopJ is incubated with human rMKK6 (or rPbs2p) and 14C-labeled acetyl-CoA in the presence and absence of candidate inhibitors for one hour at 30° C. Samples are separated by SDS-PAGE and analyzed by autoradiography to identify inhibitors that prevent O-acetylation of rMKK6 by YopJ.

The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. As used herein, the singular forms "a," "an," and "the," refer to both the singular as well as plural, unless the context clearly indicates otherwise.

REFERENCES

Deng et al., Cell 103, 351 (Oct. 13, 2000).
Gu et al., Cell 90, 595-606 (Aug. 22, 1997).
Hardie et al. *The Protein Kinase FactsBook*. G. Hardie, S. Hanks, Eds. (Academic Press Limited, San Diego, Calif., 1995), pp. 418.
Hinnebusch, Curr Issues Mol Biol 7, 197 (July, 2005).
Kalgutkar et al, J Med Chem. 1998 Nov 19;41 (24):4800-18.
Navarro, et al, Curr Opin Microbiol 8, 21 (February, 2005).
Orth, Curr Opin Microbiol 5, 38 (February, 2002).
Orth et al., Science 285, 1920 (1999).
Orth et al., Science 290, 1594 (Nov. 24, 2000).
Palmer et al, Infect Immun 67, 708 (February, 1999).
Qiang, et al. J Immunoassay & Immunochem, 26: 13-23, 2005.
Stojan et al, Eur J Biochem 271, 1364 (April, 2004).
Viboud and Bliska, Annu Rev Microbiol 59, 69 (2005).
Yoon et al, J Biol Chem 278,2131 (Jan. 24, 2003).

What is claimed is:

1. A method of detecting O-acetylation of a substrate protein of an O-acetyltransferase, comprising the step of: specifically detecting O-acetylation of a serine or threonine residue of the substrate protein.

2. The method of claim 1 wherein the specific detecting step comprises contacting the protein with an antibody that specifically binds O-acetylated serine or threonine, and determining that the antibody specifically binds the residue.

3. The method of claim 1 wherein the specific detecting step comprises by mass spectrometry analysis of the protein.

4. The method of claim 1, wherein the detected O-acetylation occurs under a first physiological condition, and is compared with a control O-acetylation that occurs under a second physiological condition.

5. The method of claim 1 wherein the O-acetylation competes with a different posttranslational modification at the residue, wherein the posttranslational modification is phosphorylation.

6. The method of claim 1 wherein the protein is selected from a MAPK kinase and IκB kinase β (IKKβ).

7. A method of detecting O-acetylation of a substrate protein of an O-acetyltransferase, comprising the steps of:
   incubating a mixture comprising the substrate protein, the O-acetyltransferase, and an acetyl donor under conditions wherein the O-acetyltransferase transfers an acetyl from the acetyl donor to a serine or threonine residue of the substrate protein to form the O-acetylation; and specifically detecting the O-acetylation of the serine or threonine residue on the substrate protein.

8. The method of claim 7 wherein the acetyl is radiolabeled.

9. The method of claim 7 wherein the acetyltransferase comprises a catalytic domain of a Clan CE cysteine protease.

10. The method of claim 7 wherein the acetyltransferase comprises a catalytic domain of a Clan CE cysteine protease from a bacterium of a genus selected from the group consisting of *Yersinia, Aeromonas, Salmonella, Vibrio, Bartonella, Ralstonia, Pseudomonas,* and *Xanthomonas*.

11. The method of claim 7 wherein the mixture further comprises a candidate agent, and the specifically detected O-acetylation is reduced relative to a control, identifying the candidate agent as an inhibitor of the O-acetyltransferase.

12. The method of claim 7 wherein the mixture further comprises an O-acetyltransferase inhibitor, and the specifically detected O-acetylation is reduced relative to a control.

13. The method of claim 11 or 12, wherein detecting step comprises specifically detecting a physiological change predetermined to be correlated with the reduced O-acetylation.

* * * * *